United States Patent [19]

Miraki et al.

[11] Patent Number: 5,074,845
[45] Date of Patent: Dec. 24, 1991

[54] CATHETER WITH HEAT-FUSED BALLOON WITH WAIST

[75] Inventors: Manouchehr Miraki, Santa Ana; Carmen Diaz, Stanton, both of Calif.

[73] Assignee: Baxter International Inc., Deerfield, Ill.

[21] Appl. No.: 677,608

[22] Filed: Mar. 27, 1991

Related U.S. Application Data

[63] Continuation of Ser. No. 381,878, Jul. 18, 1989, abandoned.

[51] Int. Cl.$^5$ ............................................. A61M 29/00
[52] U.S. Cl. ..................................... 604/101; 606/194
[58] Field of Search ................................ 606/191–194; 604/96–103, 264, 271, 280

[56] References Cited

U.S. PATENT DOCUMENTS

| | | | |
|---|---|---|---|
| 4,243,040 | 1/1981 | Beecher | 604/271 |
| 4,479,497 | 10/1984 | Fogarty et al. | 604/103 |
| 4,526,175 | 7/1985 | Chin et al. | 604/271 |
| 4,775,371 | 10/1988 | Mueller, Jr. | 604/280 |
| 4,819,664 | 4/1989 | Nazari | 604/96 |
| 4,820,270 | 4/1989 | Hardcastle et al. | 604/101 |

Primary Examiner—C. Fred Rosenbaum
Assistant Examiner—William W. Lewis
Attorney, Agent, or Firm—Sandra S. Schultz; Michael C. Schiffer

[57] ABSTRACT

Disclosed is an everting balloon catheter in which the balloon has a waist at the desired eversion point to minimize the size of the distal tip of the catheter during insertion. Preferably, the distal end of the outer body is bevelled and the waist is located just distal and radial to the tip of the outer body when the inner body is fully extended distal to the outer body. Usually, the waist is formed by heat shrinking the balloon during manufacture, thus usually increasing balloon thickness at the waist.

Also, in the disclosed invention, the balloon is attached to the outer catheter bod via heat fusion. Generally, the outer body and the balloon are both formed of compositions having at least one component in common to promote heat fusion for attachment of the balloon. Preferably that component is polyethylene.

14 Claims, 3 Drawing Sheets

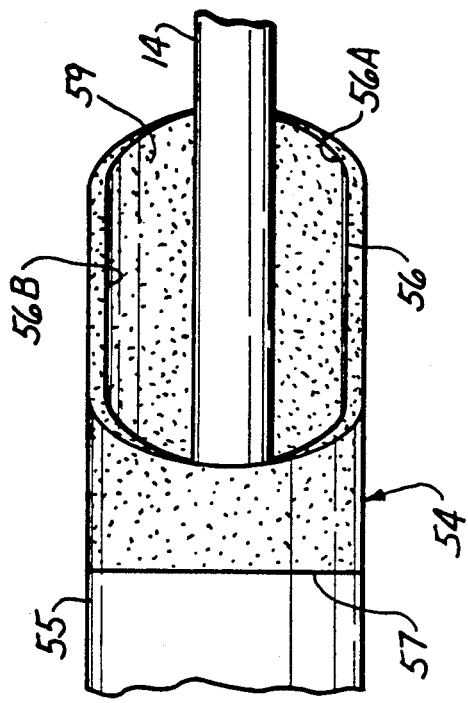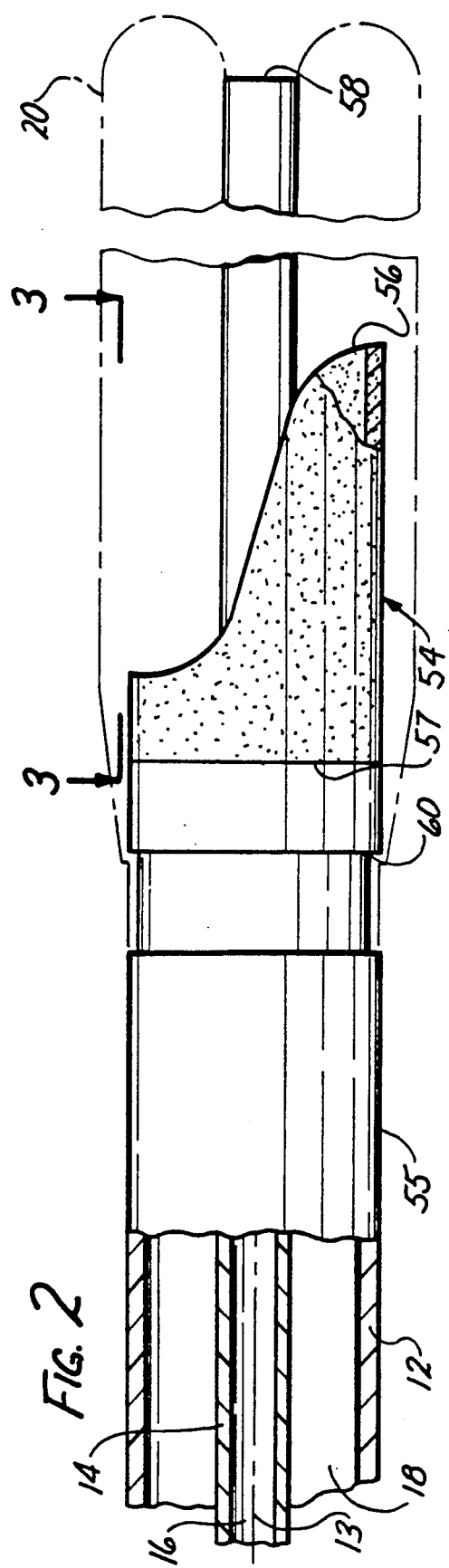

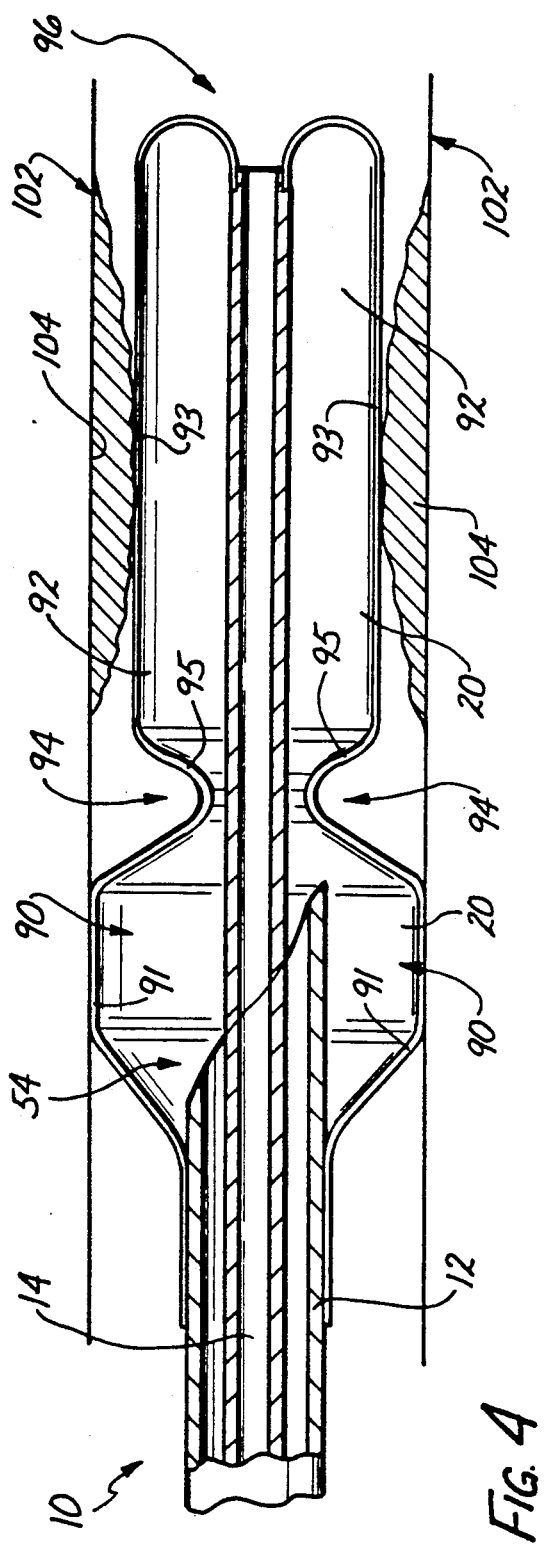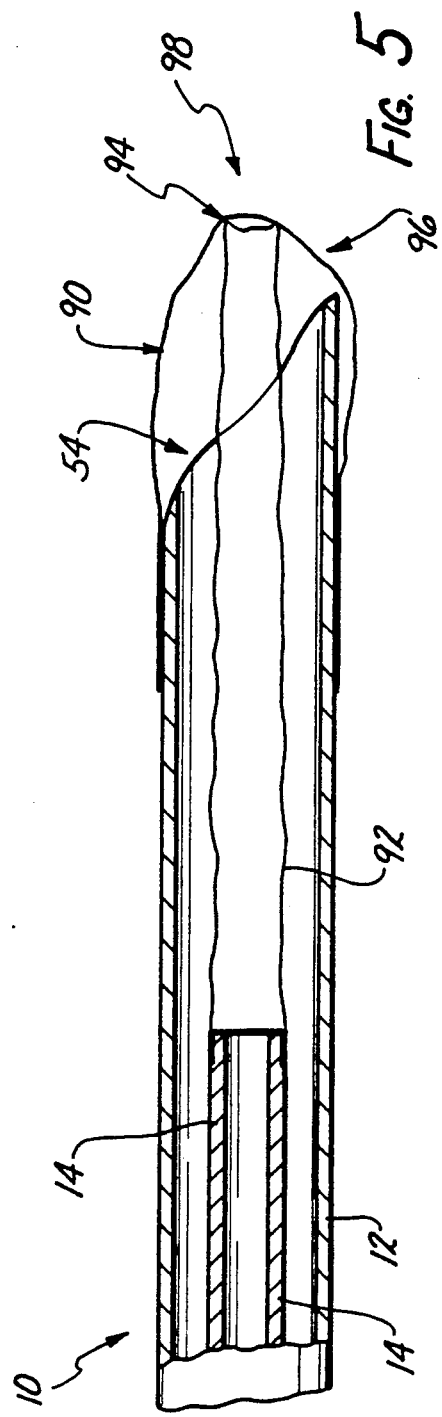

CATHETER WITH HEAT-FUSED BALLOON WITH WAIST

This is a continuation, division, of application Ser. No. 07/381,878 filed on July 18, 1989, now abandoned.

BACKGROUND OF THE INVENTION

1. Field of the Invention

This invention relates to catheters and materials for catheters, particularly everting thru-lumen balloon catheters with flexible balloons. The invention is particularly useful in catheters for dilatation, the inflation and/or repeated inflation of a balloon within a plaque occlusion or stenosis to reform the plaque deposit against the vessel wall and open the vessel.

2. Description of the Prior Art

Balloon catheters and everting balloon catheters are known in the art. For example, as disclosed in U.S. Pat. Nos. 4,437,857, 4,604,094 and 4,530,698, method and apparatus for everting a balloon using a balloon material substantially more flexible than that of the catheter body is known. Flexible but non-elastomeric balloon materials such as polyethylene are used for the balloons as disclosed in U.S. Pat. Nos. 4,493,711 and 4,606,347.

The use of an internal, slidable, tubular sheath to enhance the eversion process is shown in EPO Patent Application 86630101.1 and a seal for the thru-lumen is shown in U.S. Pat. No. 4,606,347. Also, U.S. Pat. Nos. 4,526,175 and 4,689,041 show different balloon structures.

Methods and apparatus for everting a tube are shown in U.S. Pat. No. 3,506,011. As shown in U.S. Pat. No. 4,271,839, the use of a balloon attached to slidable thru-lumen tubing or reinversion member at one end of the balloon and to the catheter body at the other end Express Mail Label No. RB310995113 of the balloon so that the balloon is everted by sliding the thru-lumen tubing distally is known for dilatation.

A problem, though, with standard designs for such a thru-lumen everting balloon is that the inverted balloon tends to result in a large, if not flared, catheter tip, difficult to slide through the tortuous pathways of the vascular system. Finally, prior art dilatation balloons are normally attached to the outer catheter body by adhesives, which frequently result in leakage and bond deterioration during inflation.

SUMMARY OF THE INVENTION

In one aspect, the invention is an everting balloon catheter having an outer tubular catheter body with a distal end, an inner tubular body with a distal end which is axially disposed internal to the outer body. A balloon is attached at its first end to the distal end of the inner body and at its second end to the distal end of the outer body, the balloon having a waist at the desired eversion point to minimize balloon flaring at the distal tip of the catheter, and preferably creating a bullet-shaped tip. Preferably, the distal end of the outer body is bevelled and the waist is located just distal and radial to the tip of the outer body when the inner body is fully extended distal to the outer body. Usually, the waist is formed by heat shrinking the balloon during manufacture, increasing balloon thickness at the waist.

In another aspect, the invention is a balloon for an everting balloon catheter having an anchor annulus. Such a catheter is fully described in U.S. patent application Ser. No. 244,978, incorporated herein by reference in its entirety. Basically, in such a catheter, an anchor annulus is formed from part of the expandable tubular balloon; the balloon is attached at its first end to the distal tip of the inner tube of the catheter, and at its second end to the outside of the outer tube of the catheter and spaced from the distal tip of that outer tube. Upon inflation of the balloon through the outer lumen, expansion of the balloon occurs radially with respect to the axis of the outer unit to anchor the catheter in place while the balloon then extends axially through an occlusion for use in dilatation. In the present invention, the waist defines the point of separation of the anchor annulus and the extending portion of the balloon.

In another aspect, the invention is an everting balloon catheter with an anchor annulus having the balloon attached to the outer body via heat fusion. Generally, the outer body and the balloon are both formed on compositions having at least one component in common to promote heat fusion for attachment of the balloon. Preferably that component is polyethylene.

BRIEF DESCRIPTION OF THE DRAWINGS

FIG. 2 is an axial plan view, partly in cross-section, of the distal end area of the catheter shown in FIG. 1 with the balloon, shown in shadow, being fully inflated and everted.

FIG. 3 is a plan view taken generally along line 3—3 of FIG. 2.

FIG. 4 is a cross-sectional detailed view of the balloon and distal tip of the catheter shown in FIG. 2 with the balloon fully everted in the vascular system.

FIG. 5 is similarly a cross-sectional detailed view of the distal end of the catheter, with balloon in fully inverted position, showing the bullet tip of the catheter.

DETAILED DESCRIPTION OF THE SPECIFIC EMBODIMENTS

Figure 1:
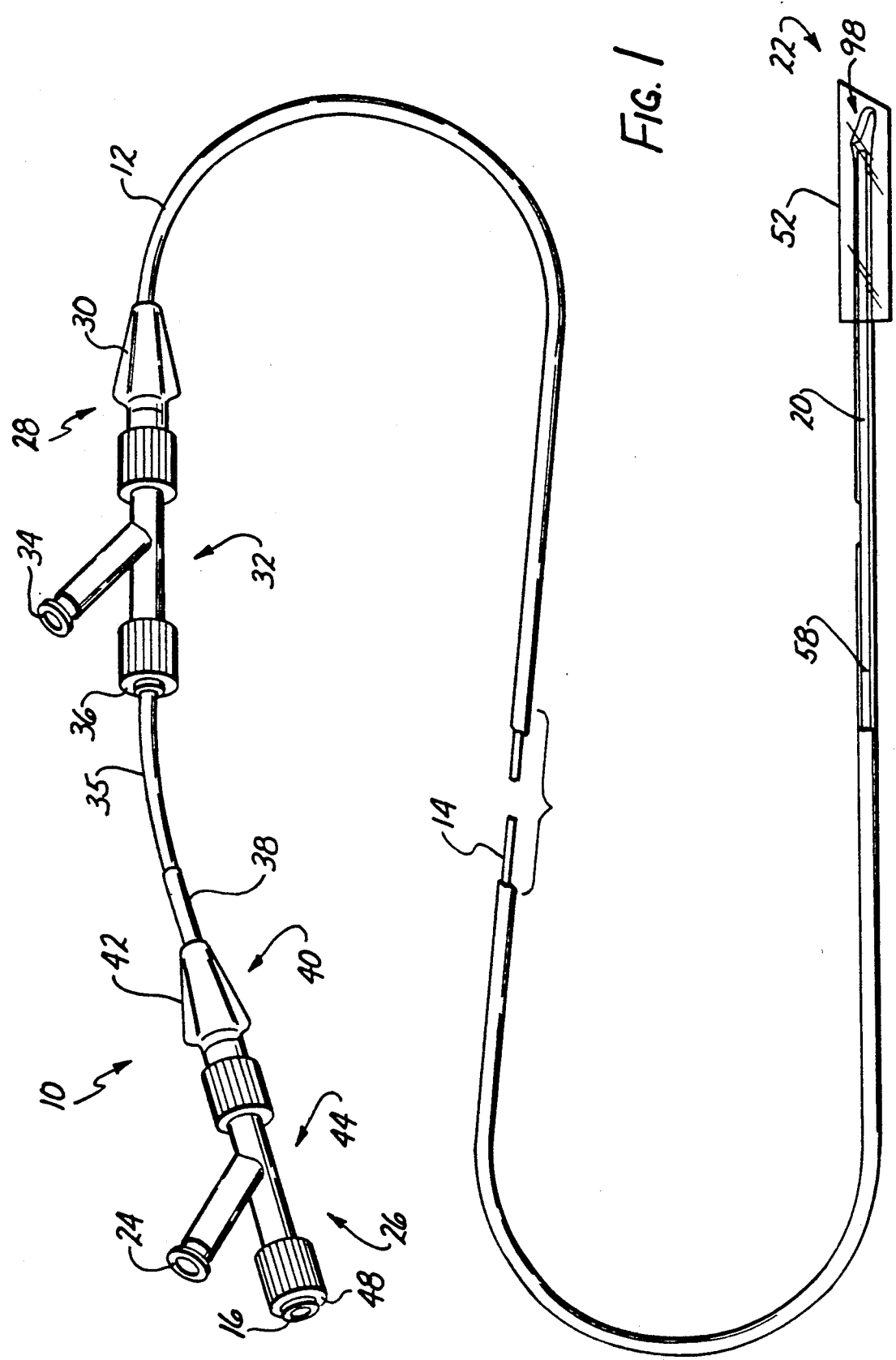
FIG. 1 is an overall view of one embodiment of the catheter of the present invention with cut-away section of the distal end portion showing the catheter balloon fully inverted.

Referring now to FIGS. 1 and 2, a linear everting balloon catheter with anchor annulus, shown generally as 10, is a dilatation catheter including an outer tube 12 about 0.06 inches in outer diameter and about 135 cm. in length defining a central axis 13. The catheter 10 has a central or inner tube 14 coaxial with the outer tube 12 to form a double lumen catheter preferably about 150 cm. long, one lumen 16 (the inner or "through-lumen") axially disposed within the other lumen 18. The through-lumen 16 is as long as the outer tube 12 plus the length of balloon 20, although additional length can be added for easy maneuverability during eversion and reinversion. The through-lumen 16 is open to the environment distally and inner tube 14 is preferably about 0.02 inches in inner diameter and about 0.028 inches in outer diameter. The through-lumen 16 allows use of the catheter 10 over a guidewire, and, via injection port 24, can be used to inject dyes, contrast media, saline, or other fluids into the system.

The catheter 10 terminates at proximal end 26 in an outer hub 28 with wings 30. The outer hub 28 is attached to an outer Y-connector 32 having an inflation port 34 accessing outer lumen 18. Through an "O" ring 36 sealing outer lumen 18 from the environment at the proximal end, inner tube 14 slidably extends proximally from outer hub 28 to terminate in a sleeve 38 surrounded by an inner hub 40 having wings 42 and attached to an inner Y-connector 44 including injection port 24 which accesses the through-lumen 16. Access to the through-lumen 16 at the proximal end is gained through an O ring 48 which can form a seal.

Sleeve 38 is usually formed of heatshrunk polyvinyl chloride ("PVC") and the two hubs 28 and 40 and related adapters are usually formed of polycarbonate or PVC. Except for the distal end segment 54 to be discussed hereinafter, the outer tube 12 is preferably made of polyethylene and the inner tube 14 of polyethersulfone. The primary considerations for the material for the tubes 12 and 14 are, of course, biological inertness, inertness to saline, contrast media and other materials to be infused through the tubing, and sufficient strength, flexibility, resistance to deformity, and torquability to bend the catheter 10 through the tortuous pathways of the vascular or any other system in which it will be used without crimping or occlusion.

The catheter 10 is stored in sterile condition before use by a cover or protective sleeve 52 over the distal end region 22.

Outer tube 12 includes a distal end segment 54 which is radioopaque. In the preferred embodiment, the distal end segment includes a beveled distal rim 56 which defines a distal end opening 59 of outer tube 12. This beveling is further illustrated by considering points 56A and 56B. Points 56A and 56B are circumferentially spaced apart and are the distal most points at two locations on rim 56. Point 56A is distal of point 56B. Thus, rim 56 is beveled. Distal end segment 54 is bonded to the proximal portion 55 of outer tube 12. For the sake of illustration, this bond is shown as a single line 57 in FIG. 2, although it is preferred that this bond involve a finite bonding area. Such bonding may be accomplished through the use of adhesives, the application of heat or the like. In the preferred embodiment, the bonding is accomplished by heat application.

The inside and outside diameters of distal end segment 54 are substantially the same as the corresponding parameters of the (proximal portion 55) of outer tube 12.

Distal end segment 54 is made, preferably extruded, from a material which is compatible with, e.g., able to be bonded to, the proximal portion 55 of outer tube 12, and is radioopaque. One particularly useful material of construction for distal end segment 54 is a mixture of about 25% by weight of an ethylene vinyl acetate copolymer and about 75% by weight tantalum powder.

When inner tube 14 is in its fully withdrawn position, its distal end 58 usually terminates up to about 15 cm. back from the beveled distal rim 56. The exact distance from end 56 will vary with the particular purpose for which the catheter 10 is designed and the length of the expected occlusion in the blood vessel. Thus, in models of catheter 10 for use in the coronary arteries inner tube 14 may terminate about 2 to 4 cm. back, while in peripheral models inner tube 14 may terminate 10 cm. or more back.

One end of balloon 20 is attached to the periphery of inner tube 14 by an adhesive, usually a cyanoacrylate, at the distal end thereof. The other end of the balloon 20 is attached to the exterior of outer tube 12 spaced back from the distal end segment 54, usually in an annular recession 60 in the exterior of the outer tube 12, and usually where the bevelled tip is fused to the outer tube.

The balloon 20, which is preferably made of an ethylene vinyl acetate—polyethylene copolymer as described in U.S. patent application Ser. No. 244,978 discussed above, is heat fused to the outer tube 12 at recession 60. This form of attachment, is preferable to adhesive attachment which frequently leaks or gives way under inflation pressures. In addition, it minimizes any possible increase in diameter of the catheter at the bonding point. In order to bond the balloon by heat fusion to the outer tube, the composition of both must contain at least one component in common. Preferably, the balloon and the outer tube contain one of the following components: polyethylene, ethylene vinyl acetate copolymer, Surlyn (a trademark for an ionomer made by DuPont). In some instances, balloon 20 may be textured on the surface to promote anchoring at the desired spot in the blood vessel. When inner tube 14 is completely withdrawn, the balloon 20 remains substantially inside the outer tube 12. When inner tube 14 is moved distally, it causes the balloon 20 to evert and aids balloon inflation when saline is simultaneously infused through the inflation port 34 to inflate the balloon 20. The material used in the balloon 20 has sufficient strength to sustain the pressures required for dilatation, usually about 10 to 12 atmospheres.

Balloon 20 is shaped to promote easy insertion of the catheter and to promote anchoring of the catheter in the vessel while the remainder of the balloon is passed through the occlusion so as to be properly located for dilatation. Balloon 20 contains an anchoring portion 90 which forms an anchor annulus and an extension portion 92, as shown in FIG. 4. The anchor annulus 90 is the portion of the balloon extending circumferentially about the outer tube 12.

The balloon defines a waist 94 smaller in outer diameter than the outer diameter of either the anchor annulus 90 or the extending portion 92 of the balloon; the waist is preferably located just distal and radial to the catheter's bevelled tip. It separates the anchor annulus 90 and the extending portion 92. Preferably, the waist wall 95 is thicker than the walls 91 and 93 of the anchoring and extending portions, and it is formed by heat shrinking. As shown in FIG. 5, waist 94 provides an inversion point for the balloon, such that when the inner tube 14 is retracted, it pulls the balloon into the outer tube 12, until resistance is reached when the waist 94 is about to invert. At that point, the cathteter tip 96 is basically bullet shaped with a distal end 98 smaller in diameter than the remainder of the catheter 10 to create a streamlined tip for easier insertion through the vascular system. In addition, as shown in FIG. 4, the anchor annulus 90 of the catheter preferably is larger in diameter than the extending portion 92. This allows the balloon, if the proper size is chosen, to easily anchor in the vasculature 102 proximal to an occlusion 104, upon inflation, as explained in detail below and in U.S. patent application Ser. No. 244,978, while the extending portion 92, because it is narrower, can more easily evert through the occlusion.

Preferably, in coronary catheters, the length of the balloon is about 3 centimeters or so from the bevelled tip of the catheter, and about 10 centimeters in peripheral catheters. Usually, the overall diameters of the outer tube in coronary angioplasty catheters are 4.0 or 4.5 Fr. and 4.2 or 5.5 Fr. in the case of peripheral catheters, In general, the extending or dilatation portion 92 of the balloon 20 is sized to achieve required dilatation, and generally ranges from 2.0 to 4.0 mm in outer diameter under standard inflation pressures. The anchor annulus 90 of balloon 20 is preferably larger in outer diameter than the dilatation portion 92 at standard inflation pressures, usually by up to 30 percent. For example, in the smaller peripheral catheter mentioned above, the outer diameter of the dilatation portion 92 is about 3.0 mm, while that of the anchor annulus is about 3.3 mm. under standard pressures.

To make the catheter 10, the balloon material is extruded to form tubing and irradiated with electron-beam radiation in the fashion used for cross-linking standard balloons. The balloons are then blown and cut to size.

The inner tubing material is also extruded and cut to size, and the balloon bonded to the outer distal tip thermally or preferably by using biocompatible adhesives such as a polycyanoacrylate adhesive or a polyurethane adhesive. The tip (i.e. about 15 cm.) of the inner tubing may be separately cut of a different material such as polyethylene and fused to the proximal portion made of polyethersulfone. A mandril is passed into the balloon which is inverted by hand rolling its open end back over the mandril and around the inner tube.

Tubing from which the proximal portion 55 of outer tube 12 is made, and tubing from which the distal and segment 54 of outer tube 12 is made, are compounded, extruded and cut. These two lengths of tubing are bonded together, e.g., in a conventional manner such as by the application of heat to the overlapped ends of the lengths of tubing. Preferably, a layer of ELVAX 460 (made by DuPont and containing polyethylene) in the form of tubing is slid around the fused area to promote joinder to the balloon later.

The bevel distal rim 56 is then cut from the distal end of the bonded tube.

Using hollow stainless steel tubing as support, the inner tube 14 is backloaded into the outer tube 12 (the bonded tube) and the balloon 20 is bonded to the outer tube at the fusion area by application of heat.

A mandril is inserted, and sleeves of the final desired balloon size placed about the balloon at the desired location, i.e. at the anchor portion 90, the extending portion 92 and the waist 84; the balloon is then inflated to standard inflation pressures. Balloon waist 94 is formed by the application of heat at the appropriate location. In addition, the extended portion 92 of balloon 20 is heat shrunk to its final, narrower size. An intermediate sleeve 35 is heat shrunk about the proximal portion of inner tube 14 to provide inner tube 14 with increased stiffness. Sleeve 38 is then heatshrunk about the proximal end of the intermediate sleeve 35 and the outer hub 28 is attached to the outer tube 12 using an ethylene vinyl acetate polymeric adhesive, followed by the outer Y connector 32, the inner hub 42 and the inner Y connector 44. The package is inspected and finally sterilized and sold. In operation, the catheter 10, with balloon 20 inverted, is introduced into the vascular system, usually via a guiding catheter, particularly when used for percutaneous coronary access. Where it will be inserted only into peripheral vessels or is inserted intraoperatively, usually no guiding catheter is used, although a guidewire can be used through the through-lumen 16. The bullet shaped tip facilitates placement of the catheter by maneuvering more easily through the guiding catheter or the vasculature than the otherwise flaring balloon tip.

The distal end segment 54 of the catheter 10 is inserted as close as possible to the lesion to be removed, under fluoroscopy, and the balloon 20 is inflated with a mixture of 50 percent saline and 50 percent contrast media by volume through the inflation port 34 to about 2 atmospheres. The precise placing of catheter 10, under fluoroscopy, is advantageously facilitated since the entire distal end segment 54 is radioopaque. Thus, under fluoroscopy, one is able to effectively visualize the distal end segment 54 of catheter 10. In addition, the beveled distal rim 56 renders the distal portion of outer tube 12 more flexible than the proximal portion 55 of outer tube 12. This increased flexibility facilitates inserting catheter 10 into the vascular system.

Inner tube 14 is slid distally to evert the balloon 20 until resistance is felt, indicating that the balloon has formed an anchor annulus. If the distal end segment 54 continues to move, however, the catheter 10 is insufficiently anchored, and the balloon 20 is inflated further until the anchor annulus is formed. The more compliant the balloon material, the lower the amount of pressure required to form the anchor annulus. Silicone texturing on the exterior of the annulus may further help to anchor the catheter 10. Continuing to push the inner tube 14 distally, the narrow portion 92 of balloon 20 is then further everted to extend it until it crosses the stenosis. At that point, dilatation (or any diagnostic purpose for which the catheter 10 is inserted) is handled in the standard manner. When the process is finished, the balloon 20 is deflated (via the inflation port) and the catheter withdrawn, or the balloon 20 is reinverted after the catheter is withdrawn by pulling the inner tube 14 proximally.

It should be understood that the foregoing description is intended by way of illustration and not by way of limitation and that many modifications and variations are within the scope of the invention which is described by the appended claims. Furthermore, it should be noted that the invention relates to many different types of apparatus and catheters, not just dilatation catheters.

What is claimed is:

1. A catheter comprising
   outer and inner tubes having proximal and distal ends, said inner tube being slidable positioned in said outer tube and being dimensioned to provide a fluid passageway between said inner and outer tubes, with said outer tube distal end being bevelled; and
   a balloon formed from an expandable tubular member having first and second opposing ends with one of said ends attached to said outer tube distal end and said second end being attached to said inner tube distal end, said tubular member being dimensioned and sized to allow said inner tube to be selectively drawn into said outer tube and to be extended out of said outer tube, said tubular member further being formed at a location distal said attachment to said outer tube distal end with a waist having a diameter smaller than the remainder of said tubular member, said smaller diameter waist dividing said tubular member into a first balloon section adjacent said outer tube distal end and a second balloon section adjacent said inner tube distal end.

2. The catheter of claim 1 wherein said smaller diameter waist is formed by heat shrinking said tubular member.

3. The catheter of claim 1 wherein said tubular member is formed with an outer textured surface.

4. The catheter of claim 1 wherein said first and second balloon sections are of different diameters when expanded.

5. The catheter of claim 4 wherein said first balloon section has a diameter larger than that of said second balloon section.

6. The catheter of claim 4 wherein said smaller diameter waist is dimensioned to resist inversion when said inner tube is being drawn into said outer tube.

7. The catheter of claim 6 wherein said first balloon section has a diameter larger than that of said second balloon section.

8. The catheter of claim 7 wherein said tubular member is formed with an outer textured surface.

9. The catheter of claim 1 wherein said smaller diameter waist is dimensioned to resist inversion when said inner tube is being drawn into said outer tube.

10. A catheter comprising
    outer and inner concentrically mounted tubes having proximal and distal ends, said inner tube being slidable positioned in said outer tube and being dimensioned to provide a fluid passageway between said inner and outer tubes, with said outer tube distal end being bevelled; and
    a balloon formed from an expandable tubular member having first and second opposing ends with one of said ends attached to said outer tube distal end and said second end being attached to said inner tube distal end, said tubular member being dimensioned and sized to allow said inner tube to be selectively drawn into said outer tube and to be extended out of said outer tube, said tubular member further being formed at a location distal said attachment to said outer tube distal end with a waist having a diameter smaller than the remainder of said tubular member, said smaller diameter waist dividing said tubular member into a first balloon section adjacent said outer tube distal end and a second balloon section adjacent said inner tube distal end, with said first balloon section having a diameter when expanded larger than that of said second balloon section when expanded.

11. The catheter of claim 10 wherein said tubular member is formed with an outer textured surface.

12. The catheter of claim 10 wherein said first balloon section lies circumferentially about the outer tube distal end.

13. The catheter of claim 10 wherein said smaller diameter waist is dimensioned to resist inversion when said inner tube is being drawn into said outer tube.

14. The catheter of claim 13 wherein said tubular member is formed with an outer textured surface.

* * * * *